United States Patent [19]

Ohishi et al.

[11] Patent Number: 4,609,736

[45] Date of Patent: Sep. 2, 1986

[54] RHODANINES USEFUL AS A THERAPEUTIC AGENT FOR DIABETIC COMPLICATIONS

[75] Inventors: Yoshitaka Ohishi, Uji; Michiko Nagahara, Yasu; Yoshitaka Takehisa, Omihachiman; Motoyuki Yajima; Shigeki Kurokawa, both of Otsu; Norio Kajikawa, Kyoto; Akira Itoh, Otsu, all of Japan

[73] Assignee: Kaken Pharmaceutical Co., Ltd., Tokyo, Japan

[21] Appl. No.: 675,579

[22] Filed: Nov. 28, 1984

[30] Foreign Application Priority Data

Nov. 29, 1983 [JP] Japan .................................. 58-226488

[51] Int. Cl.$^4$ .................. C07D 277/36; A61K 31/425
[52] U.S. Cl. ...................................... 548/183; 514/369
[58] Field of Search .......................... 548/183; 514/369

[56] References Cited

U.S. PATENT DOCUMENTS 4,446,143  5/1984  Tanouchi et al. .................... 424/270
4,464,382  8/1984  Tanouchi et al. .................... 424/270

FOREIGN PATENT DOCUMENTS 45165   2/1982  European Pat. Off. ............. 548/183
47109   3/1982  European Pat. Off. ............. 548/183
334806 12/1977  U.S.S.R. ............................. 548/183

OTHER PUBLICATIONS

Tanouchi et al, Chem. Abst. 96-217830n.
Tanouchi et al, Chem. Abst. 97-23781x.
Mousseron, Chem. Abst. 72-121519w.
Duerr; Chem. Abst. 77-15623u.
Boehringer; Chem. Abst. 80-47977r.
Pollock; Chem. Abst. 97-84108t.
Tadao et al, Chem. Abst. 96-217830n.
Tadao et al, Chem. Abst. 97-23781x.
Pathak et al, Chem. Abst. 97-92183r.
Shukla et al, Chem. Abst. 97-216065a.

Primary Examiner—Donald G. Daus
Assistant Examiner—Cecilia Shen
Attorney, Agent, or Firm—Armstrong, Nikaido, Marmelstein & Kubovcik

[57] ABSTRACT

A rhodanine derivative having the following general formula (I):

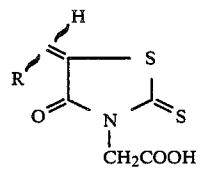

wherein R is an acyclic alkyl group having 2 to 10 carbon atoms which may be substituted by a halogen atom or an acyclic alkenyl group having 2 to 19 carbon atoms which may be substituted by a halogen atom; or a nontoxic salt thereof. The rhodanine derivative has potent platelet aggregation inhibiting activity and aldose reductase inhibiting activity and therefore is useful as a therapeutic agent for diabetic complications.

2 Claims, No Drawings

RHODANINES USEFUL AS A THERAPEUTIC AGENT FOR DIABETIC COMPLICATIONS

BACKGROUND OF THE INVENTION

The present invention relates to novel rhodanine derivatives, processes for preparing the same and a pharmaceutical composition containing the same as a therapeutic agent for diabetic complications.

In recent years, westernization of eating habits has resulted in a marked increase in the number of diabetic patients and measures for the treatment thereof are urgently needed.

As therapeutic agents for diabetes, insulin and blood sugar lowering agents have so far been used widely. However, diabetes is not a mere disorder of sugar metabolism but a disease also involving a variety of complications and therefore the therapeutic effects of the above-mentioned agents alone are not enough for the treatment of diabetes.

Among main complications, cerebral and coronary vascular disturbances account for about 50% of causes of deaths resulting from diabetes [Y. Goto et al., Sogo Rinsho, 22, 779 to 785 (1973)].

Blood platelets play an important role in the development of such vascular disturbances. Thus, in a diabetic condition, platelets are in the state of hyperfunction, causing thrombosis and at the same time arteriosclerosis [H. Heath et al., Diabetologia, 7, 308 to 315 (1971)]. Therefore, platelet aggregation inhibitors are useful in the treatment of vascular disturbance such as mentioned above.

On the other hand, diseases of the eye, such as retinopathy and cataract, are also important diabetic complications and form the primary cause of blindness of the aged. In the development of such diseases, not only disturbances of retinal and other blood vessels, namely microangiopathy, is an important pathogenic factor, but also a certain kind of sugar metabolism disorder is concerned [K. H. Gabbay, Adv. Metab. Disord., 2(2), 424 1973)]. Thus, in the diabetic condition, polyols such as sorbitol are accumulated to an extraordinary extent, causing osmotic pressure increase and water retention, which lead to ocular tissue disturbance. Therefore, inhibition of aldose reductase which is essential to polyol synthesis can possibly be effective in the prevention and treatment of the above-mentioned diseases of the eye [R. G. Judzewitsch et al., New Eng. J. Med., 308, 119 to 125 (1983); J. H. Kinoshita et al., Metabolism, 28 (1), 462 to 469 (1979)].

SUMMARY OF THE INVENTION

It is an object of the present invention to provide a novel compound useful as a therapeutic agent for diabetic complications including perceptual disorder, autonomic disturbance, diabetic nephropathy, and ocular diseases such as retinopathy and cataract.

This and other objects of the present invention will become apparent from the description hereinafter.

DETAILED DESCRIPTION

The present invention provides a rhodanine derivative having the following general formula (I):

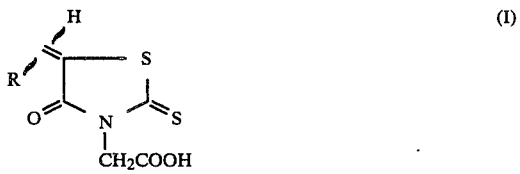

wherein R is an acyclic alkyl group having 2 to 10 carbon atoms which may be substituted by a halogen atom or an acyclic alkenyl group having 2 to 19 carbon atoms which may be substituted by a halogen atom; and a nontoxic salt thereof.

Examples of the halogen atom which may be contained in the acyclic alkyl or alkenyl group as the group R in the formula (I) are fluorine, chlorine, bromine and iodine.

Examples of the acyclic alkyl group as the group R in the formula (I) are, for instance, ethyl, 3-chloropropyl, t-butyl, n-decyl and n-pentyl groups. Examples of the acyclic alkenyl group as the group R in the formula (I) are, for instance, vinyl, 1-propenyl, 3-chloro-1-propenyl, 2-methyl-1-propenyl, 1-pentenyl, 1,3-pentadienyl, 2,6-dimethyl-1,5-heptadienyl and 2,6,10,14-tetramethyl-1,5,9,13-pentadecatetraenyl groups.

Examples of the nontoxic salts of the rhodanine derivative (I) are pharmaceutically acceptable salts, for instance, metal salts such as sodium salt, potassium salt, magnesium salt and calcium salt; salts with amine compounds such as methylamine, dimethylamine, ethanolamine, allylamine, isobutylamine, hexylamine, morpholine and methylpiperazine, mineral acid salts such as hydrochloride and sulfate.

The rhodanine derivative (I) includes any of trans form, cis form and mixture of these isomers.

The compounds represented by the general formula (I) and nontoxic salts thereof as provided by the present invention have potent platelet aggregation inhibiting activity which is 10 times that of Persantine (dipyridamole by generic name) which is an anti-platelet aggregation agent in widest use. At the same time, they have potent aldose reductase inhibiting activity and very low toxicity. Therefore, they can serve as excellent therapeutic agents for diabetic complications.

The preferred compounds among the compounds represented by the general formula (I) are shown in Table 1.

TABLE 1

| Compound No. | Formula | Name |
|---|---|---|
| 1 | CH₃CH₂CH= (rhodanine with NCH₂COOH) | 3-Carboxymethyl-5-propylidenerhodanine |
| 2 | Cl(CH₂)₃CH= (rhodanine with NCH₂COOH) | 3-Carboxymethyl-5-(4-chlorobutylidene)rhodanine |
| 3 | (CH₃)₃C—CH= (rhodanine with NCH₂COOH) | 3-Carboxymethyl-5-(2,2-dimethylpropylidene)rhodanine |
| 4 | CH₃(CH₂)₉CH= (rhodanine with NCH₂COOH) | 3-Carboxymethyl-5-undecylidenerhodanine |
| 5 | CH₃CH₂CH₂CH₂CH₂CH= (rhodanine with NCH₂COOH) | 3-Carboxymethyl-5-n-hexylidenerhodanine |
| 6 | CH₂=CHCH= (rhodanine with NCH₂COOH) | 3-Carboxymethyl-5-allylidenerhodanine |
| 7 | CH₃—CH=CH—CH= (rhodanine with NCH₂COOH) | 3-Carboxymethyl-5-(2-butenylidene)rhodanine |
| 8 | ClCH₂CH=CHCH= (rhodanine with NCH₂COOH) | 3-Carboxymethyl-5-(4-chloro-2-butenylidene)rhodanine |
| 9 | (CH₃)₂C=CH—CH= (rhodanine with NCH₂COOH) | 3-Carboxymethyl-5-(3-methyl-2-butenylidene)rhodanine |

TABLE 1-continued

| Compound No. | Formula | Name |
|---|---|---|
| 10 | CH₃CH₂CH₂CH=CHCH= (rhodanine ring with NCH₂COOH) | 3-Carboxymethyl-5-(2-hexenylidene)rhodanine |
| 11 | CH₃CH=CHCH=CHCH= (rhodanine ring with NCH₂COOH) | 3-Carboxymethyl-5-(2,4-hexadienyliene)rhodanine |
| 12 | (CH₃)₂C=CHCH₂CH₂C(CH₃)=CH—CH= (rhodanine ring with NCH₂COOH) | 3-Carboxymethyl-5-(3,7-dimethyl-2,6-octadienylidene)rhodanine |
| 13 | (CH₃)₂C=C—(CH₂)₂C(CH₃)=CH(CH₂)₂C(CH₃)=CH(CH₂)₂C(CH₃)=CHCH= (rhodanine ring with NCH₂COOH) | 3-Carboxymethyl-5-(3,7,11,15-tetramethyl-2,6,10,14-hexadecatetraenylidene)-rhodanine |

Japanese Patent Application Kokai Tokkyo Koho Nos. 57-28074 and 57-40478, corresponding to U.S. Pat. Nos. 4,446,143 and 4,464,382 respectively, disclose some rhodanine derivatives for use as aldose reductase inhibitors. However, between the rhodanine derivatives described in the above-cited publications and the rhodanine derivatives of the invention, there is a substantial difference in the substituent at position 5. Moreover, the rhodanine derivatives of the invention have especially potent platelet aggregation inhibiting activity. The publications cited above mention nothing of such activity. Thus the rhodanine derivatives of the invention have a wide application range in clinical field.

Among the rhodanine derivatives of the invention, the 2-allylidene derivative (Compound No. 6), the 4-chloro-2-butenylidene derivative (Compound No. 8), the 2-butenylidene derivative (Compound No. 7), the 2-hexenylidene derivative (Compound No. 10), the 2,4-hexadienylidene derivative (Compound No. 11) and the 3,7,11,15-tetramethyl-2,6,10,14-hexadecatetraenylidene derivative (Compound No. 13) have a noticeably strong platelet aggregation inhibiting activity.

The rhodanine derivatives (I) of the present invention are prepared by reacting 3-carboxymethylrhodanine having the following formula (II):

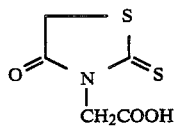
(II)

or a salt thereof with an aldehyde compound having the following general formula (III):

$R^1$—CHO  (III)

wherein $R^1$ is an acyclic alkyl group having 1 to 9 carbon atoms which may be substituted by a halogen atom or an acyclic alkenyl group having 2 to 18 carbon atoms which may be substituted by a halogen atom.

Concretely, 3-carboxymethylrhodanine or its salt is dissolved into a solvent such as acetone, dimethylformamide (hereinafter referred to as "DMF"), dimethyl sulfoxide (hereinafter referred to as "DMSO") or acetic acid. To the solution is added an alkali catalyst such as potassium carbonate, sodium hydroxide or sodium acetate. The amount of the catalyst used is preferably from 1 to 2 moles per 1 mole of 3-carboxymethylrhodanine. An aldehyde compound (III) is added to the mixture dropwise at room temperature or under heating at 50° to 90° C. The amount of the aldehyde compound used is preferably from 1 to 1.5 moles per 1 mole of 3-carboxymethylrhodanine. The obtained mixture is agitated at a temperature of from room temperature to 120° C. for 1 to 24 hours. After the reaction is completed, the reaction mixture is poured into water and the resultant is extracted with an appropriate organic solvent such as ethyl acetate. The extract is purified in a usual manner such as silica gel column chromatography or recrystallization to give a rhodanine derivative (I).

The rhodanine derivatives and nontoxic salts thereof according to the invention are useful in the prevention or treatment of diabetic complications such as diseases of circulatory organs due to their excellent platelet aggregation inhibiting activity, and also useful in the prevention or treatment of nervous disturbance resulting from abnormal accumulation of polyols, diabetic retinopathy and cataract due to their excellent aldose reductase inhibiting activity. The effect on such prevention and treatment can be sufficiently exhibited by the dosage of about 0.05 to about 200 mg/day to adult.

The rhodanine derivatives (I) and nontoxic salt thereof can be formulated into pharmaceutical compositions in the form of tablets, capsules, injections, powders, pills, granules, suppositories and eye drops. Such preparations can be prepared in a usual manner using conventional pharmaceutically acceptable carriers. Examples of the carrier are, for instance, excipients, binders, diluents and lubricants. Typical examples thereof are lactose, starch, sugar, microcrystalline cellulose, magnesium stearate, silicon dioxide, talc, physiological salt solution and sterilized water.

The present invention is more specifically described and explained by means of the following Examples. It is to be understood that the present invention is not limited to the Examples, and various change and modifications may be made in the invention without departing from the spirit and scope thereof.

The abbreviations in the Examples mean the followings:
MP: Melting point
EA: Elementary analysis
IR: Infrared absorption spectrum ($\nu_{max}^{KBr}$ cm$^{-1}$)
MS: Mass spectrum (20 eV, Direct)
NMR: Proton nuclear magnetic resonance spectrum (in DMSO-d$_6$, δ(ppm))

In addition, the proton in the group represented by the formula "—CH=(Rh)" in NMR spectra means the proton of the group "—CH=" which is directly attached to the 5-position of 3-carboxymethylrhodanine.

EXAMPLE 1

[3-Carboxymethyl-5-(2,2-dimethylpropylidene)rhodanine (Compound No.3)]

Into 20 ml of dry DMF was dissolved 1.5 g (0.008 mole) of 3-carboxymethylrhodanine. To the solution was added 2.2 g (0.016 mole) of K$_2$CO$_3$ at a room temperature, and further 1 g (0.012 mole) of 2,2-dimethylpropanal was added dropwise at 60° C. After agitating at 60° C. for 30 minutes, the reaction mixture was poured into water. The resultant was adjusted to pH 4 with a dilute hydrochloric acid and then extracted with ethyl acetate. The extract was purified through a silica gel column and recrystallized from a mixed solvent of ethyl acetate and ethanol to give 1.3 g of 3-carboxymethyl-5-(2,2-dimethylpropylidene)rhodanine in the form of light yellow needle (yield: 63%).

The characteristic properties of the product are as follows:
MP: 160° to 163° C. (from ethyl acetate-ethanol)
IR (cm$^{-1}$): 3300 to 3100 (COOH), 1730 (ring C=O)
MS (m/e): 259 (M$^+$), 241 (M$^+$—H$_2$O), 213 (M$^+$—COOH)
NMR (ppm): 1.17 (9H, s, C(CH$_3$)$_3$), 4.69 (2H, s, >NCH$_2$—), 6.88 (1H, s, —CH=), 9.81 (1H, bs, COOH)
EA for C$_{10}$H$_{13}$O$_3$NS$_2$ (MW=259.348): Calcd. (%): C 46.31; H 5.05; N 5.40; Found (%): C 46.50; H 5.21; N 5.53

EXAMPLE 2

[3-Carboxymethyl-5-(2,4-hexadienylidene)rhodanine (Compound No.11)]

4 Grams (0.021 mole) of 3-carboxymethylrhodanine was dissolved into 30 ml of acetic acid. To the solution were added 2 g (0.021 mole) of hexa-2,4-dienal and 3.8 g (0.046 mole) of sodium acetate, and the resultant was stirred under mild reflux for 5 hours. The obtained black reaction mixture was concentrated to about one-half its initial volume under reduced pressure. The residual mixture was poured into water to form precipitate. The precipitate was extracted with ethyl acetate and the extract was recrystallized from a mixed solvent of methylene chloride and ethyl acetate to give 4.1 g of 3-carboxymethyl-5-(2,4-hexadienylidene)rhodanine in the form of yellow prism (yield: 73%).

The characteristic properties of the product are as follows:
MP: 214° to 216° C. (decomposition) (from methylene chloride-ethyl acetate)
IR (cm$^{-1}$): 3050 to 3200 (COOH), 1730 (ring C=O)
MS (m/e): 269 (M$^+$), 251 (M$^+$—OH), 223 (M$^+$—COOH)
NMR (ppm): 1.71 (3H, d, CH$_3$), 4.40 (2H, s, >NCH$_2$—), 5.60 to 6.70 (4H, m, —CH=CH—CH=CH—), 7.01 (1H, d, —CH=(Rh)), 8.30 (1H, bs, —COOH)
EA for C$_{11}$H$_{11}$O$_3$NS$_2$ (MW=269.344): Calcd. (%): C 49.05; H 4.12; N 5.20; Found (%): C 48.90; H 4.19; N 5.35

EXAMPLE 3

[3-Carboxymethyl-5-propylidenerhodanine (Compound No.1)]

The same procedures as in Example 2 except that propionaldehyde was used instead of hexa-2,4-dienal were repeated to give 3-carboxymethyl-5-propylidenerhodanine (yield: 67%).

The characteristic properties of the product are as follows:
MP: 138° to 140° C.
IR (cm$^{-1}$): 3150 (COOH), 1720 (ring C=O)
MS (m/e): 231 (M$^+$), 213 (M$^+$—OH), 185 (M$^+$—COOH)
NMR (ppm): 6.05 (3H, t, CH$_3$), 2.15 (2H, m, CH$_3$CH$_2$—), 4.38 (2H, s, >NCH$_2$—), 6.59 (1H, t, —CH=), 8.05 (1H, bs, COOH)
EA for C$_8$H$_9$NO$_3$S$_2$ (MW=231.294): Calcd. (%): C 41.54; H 3.92; N 6.06; Found (%): C 41.68; H 3.99; N 6.28

EXAMPLE 4

[3-Carboxymethyl-5-(4-chlorobutylidene)rhodanine (Compound No.2)]

The same procedures as in Example 2 except that 4-chlorobutyraldehyde was used instead of hexa-2,4-dienal were repeated to give the desired product (yield: 76%).

The characteristic properties of the product are as follow:

MP: 155° to 157° C.

IR (cm$^{-1}$): 3180 (COOH), 1734 (ring C=O), 1635 (COOH)

MS (m/e): 279 (M+), 261 (M+—OH), 243 (M+—HCl), 233 (M+—COOH)

NMR (ppm): 1.90 (2H, m, ClCH$_2$CH$_2$CH$_2$—), 2.32 (2H, q, —CH$_2$—CH=), 3.54 (2H, t, ClCH$_2$—), 4.51 (2H, s, >NCH$_2$—), 6.78 (1H, d, CH$_2$CH=), 8.10 (1H, bs, COOH)

EA for C$_9$H$_{10}$NO$_3$S$_2$Cl (MW=279.766): Calcd. (%): C 38.64; H 3.60; N 5.01; Found (%): C 38.51; H 3.77; N 5.21

EXAMPLE 5

[3-Carboxymethyl-5-undecylidenerhodanine (Compound No.4)]

The same procedures as in Example 2 except that undecanealdehyde was used instead of hexa-2,4-dienal were repeated to give the desired compound (yield: 79%).

The characteristic properties of the product are as follows:

MP: 61° to 63° C.

IR (cm$^{-1}$): 2950 (COOH), 1730 (ring C=O)

MS (m/e): 343 (M+), 204 (M+—CH$_3$(CH$_2$)$_8$)

NMR (ppm): 0.82 (3H, bd, CH$_3$), 1.20 (16H, bs, CH$_3$CH$_2$(CH$_2$)$_8$—), 2.16 (2H, bq, CH$_3$CH$_2$—), 4.49 (2H, s, >NCH$_2$—), 6.72 (1H, t, —CH=), 8.20 (1H, bs, COOH)

EA for C$_{16}$H$_{25}$NO$_3$S$_2$ (MW=343.510): Calcd. (%): C 55.95; H 7.34; N 4.08; Found (%): C 56.16; H 7.19; N 4.20

EXAMPLE 6

[3-Carboxymethyl-5-n-hexylidenerhodanine (Compound No.5)]

The same procedures as in Example 2 except that hexanal was used instead of hexa-2,4-dienal were repeated to give the desired product (yield: 75%).

The characteristic properties of the product are as follows:

MP: 136° to 140° C. (from n-hexane)

IR (cm$^{-1}$): 3430 (COOH), 1715 (ring C=O)

MS (m/e): 273 (M+), 227 (M+—COOH), 204 (M+—CH$_3$(CH$_2$)$_4$)

NMR (ppm): 0.84 (3H, bt, CH$_3$), 1.05 to 1.70 (6H, m, CH$_3$(CH$_2$)$_3$—), 2.18 (2H, bq, —CH$_2$—CH=), 4.56 (2H, s, >NCH$_2$—), 6.98 (1H, t, —CH=), 8.70 (1H, bs, COOH)

EA for C$_{11}$H$_{15}$NO$_3$S$_2$ (MW=273.360): Calcd. (%): C 48.33; H 5.53; N 5.12; Found (%): C 48.22; H 5.60; N 5.01

EXAMPLE 7

[3-Carboxymethyl-5-allylidenerhodanine (Compound No.6)]

The same procedures as in Example 2 except that acrolein was used instead of hexa-2,4-dienal were repeated to give the desired compound (yield: 67%).

The characteristic properties of the product are as follow:

MP: 144° to 146° C.

IR (cm$^{-1}$): 3430 (COOH), 1735 (ring C=O)

MS (m/e): 229 (M+), 112

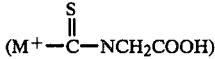

(M+—C(=S)—NCH$_2$COOH)

NMR (ppm): 4.39 (2H, s, >NCH$_2$—), 5.50 (1H, dd,

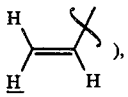

), 5.69 (1H, dd,

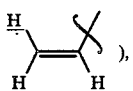

), 6.10 (1H, m, H$_2$C=CH—),
6.98 (1H, d, —CH=(Rh)), 8.52 (1H, bs, COOH)

EA for C$_8$H$_7$NO$_3$S$_2$ (MW=229.278): Calcd. (%): C 41.91; H 3.08; N 6.11; Found (%): C 41.76; H 2.88; N 6.25

EXAMPLE 8

[3-Carboxymethyl-5-(2-butenylidene)rhodanine (Compound No.7)]

The same procedures as in Example 2 except that 2-butenal was used instead of hexa-2,4-dienal were repeated to give the desired compound (yield: 80%).

The characteristic properties of the product are as follows:

MP: 216° to 218° C. (from ethanol-water)

IR (cm$^{-1}$): 3140 (COOH), 1737 (ring C=O), 1686 (COOH)

MS (m/e): 243 (M+), 225 (M+—OH), 197 (M+—COOH)

NMR (ppm): 1.82 (3H, d, CH$_3$), 4.45 (2H, s, >NCH$_2$—), 6.05 (1H, dd, —CH=CH—), 6.35 (1H, m, CH$_3$CH=), 7.18 (1H, d, —CH=(Rh)), 8.03 (1H, bs, COOH)

EA for C$_9$H$_9$NO$_3$S$_2$ (MW=243.290): Calcd. (%): C 44.43; H 3.73; N 5.76; Found (%): C 44.35; H 3.83; N 5.64

EXAMPLE 9

[3-Carboxymethyl-5-(4-chloro-2-butylidene)rhodanine (Compound No.8)]

The same procedures as in Example 2 except that 4-chloro-2-butenal was used instead of hexa-2,4-dienal were repeated to give the desired compound (yield: 85%).

The characteristic properties of the product are as follows:

MP: 205° to 207° C. (purified by column chromatography)

IR (cm$^{-1}$): 3150 (COOH), 1739 (ring C=O), 1677 (COOH)

MS (m/e): 277 (M+), 259 (M+—OH), 243 (M+—Cl), 231 (M+—COOH), 228 (M+—ClCH$_2$)

NMR (ppm): 4.20 (2H, d, ClCH$_2$—), 4.48 (2H, s, NCH$_2$—), 6.30 to 6.54 (2H, m —CH=CH—), 7.26 (1H, d, —CH$_2$=(Rh))

EA for C$_9$H$_8$NO$_3$S$_2$Cl (MW=277.750): Calcd. (%): C 38.92; H 2.90; N 5.04; Found (%): C 38.69; H 2.83; N 5.14

EXAMPLE 10

[3-Carboxymethyl-5-(3-methyl-2-butenylidene)rhodanine (Compound No.9)]

The same procedures as in Example 2 except that 3-methyl-2-butenal was used instead of hexa-2,4-dienal were repeated to give the desired compound (yield: 57%).

The characteristic properties of the product are as follow:

MP: 206° to 210° C. (decomposition)

IR (cm$^{-1}$): 3220 (COOH), 1737 (ring C=O), 1697 (COOH)

MS (m/e): 257 (M+), 239 (M+—OH), 212 (M+—COOH)

NMR (ppm): 1.88 (6H, s, (CH$_3$—)×2), 4.48 (2H, s, >NCH$_2$—), 5.82 (1H, d, (CH$_3$)$_2$C=CH—), 7.30 (1H, d, —CH=(Rh)), 8.80 (1H, bd, COOH)

EA for C$_{10}$H$_{11}$NO$_3$S$_2$ (MW=257.320): Calcd. (%): C 46.67; H 4.31; N 5.44; Found (%): C 46.70; H 4.31; N 5.40

EXAMPLE 11

[3-Carboxymethyl-5-(2-hexenylidene)rhodanine (Compound No.10)]

The same procedures as in Example 2 except that 2-hexenal was used instead of hexa-2,4-dienal were repeated to give the desired compound (yield: 71%).

The characteristic properties of the product are as follows:

MP: 188° to 190° C.

IR (cm$^{-1}$): 3100 (COOH), 1724 (ring C=O)

MS (m/e): 271 (M+), 253 (M+—OH), 225 (M+—COOH)

NMR (ppm): 0.85 (3H, t, CH$_3$), 1.40 (2H, m, CH$_3$CH$_2$—), 2.14 (2H, q, CH$_3$CH$_2$CH$_2$—), 4.49 (2H, s, >NCH$_2$—), 5.98 (1H, m, olefinic proton), 6.36 (1H, m, olefinic proton), 7.10 (1H, d, —CH=(Rh)), 9.10 (1H, bs, COOH)

EA for C$_{11}$H$_{13}$NO$_3$S$_2$ (MW=271.334): Calcd. (%): C 48.69; H 4.83; N 5.16; Found (%): C 48.44; H 5.03; N 5.19

EXAMPLE 12

[3-Carboxymethyl-5-(3,7-dimethyl-2,6-octadienylidene)rhodanine (Compound No.12)]

The same procedures as in Example 2 except that 3,7-dimethyl-2,6-octadienal was used instead of hexa-2,4-dienal were repeated to give the desired compound (yield: 65%).

The characteristic properties of the product are as follows:

MP: 95° to 98° C.

IR (cm$^{-1}$): 3400 (COOH)

MS (m/e): 325 (M+), 282 (M+—(CH$_3$)$_2$—CH), 257 (M+—(CH$_3$)$_2$CH=CHCH$_2$)

NMR (ppm): 1.55 (3H, bs, terminal CH$_3$), 1.58 (3H, bs, terminal CH$_3$), 1.85 (4H, m, —CH$_2$CH$_2$—), 1.92 (3H, s, $$-\underset{\underset{CH_3}{|}}{C}=),$$

4.85 (2H, s, >NCH$_2$—), 4.98 (1H, m, (CH$_3$)$_2$C=C$\underline{H}$—), 5.88 (0.5H, bd, $$\underset{\underset{|}{C}H_3}{\overset{|}{}}$$
$$-C=C\underline{H}-CH=),$$

6.01 (0.5H, bd, $$\underset{\underset{|}{C}H_3}{\overset{|}{}}$$
$$-C=C\underline{H}-CH=),$$

7.38 (0.5H, bd, —CH=(Rh)), 7.50 (0.5H, bd, —CH=(Rh)), 8.10 (1H, bs, COOH)

EA for C$_{15}$H$_{19}$NO$_3$S$_2$ (MW=325.430): Calcd. (%): C 55.36; H 5.89; N 4.30; Found (%): C 55.50; H 5.95; N 4.20

EXAMPLE 13

[3-Carboxymethyl-5-(3,7,11,15-tetramethyl-2,6,10,14-hexadecatetraenylidene)rhodanine (Compound No.13)]

The same procedures as in Example 2 except that 3,7,11,15-tetramethyl-2,6,10,14-hexadecatetraenal was used instead of hexa-2,4-dienal were repeated to give the desired compound (yield: 54%).

The characteristic properties of the product are as follows:

MP: 35° to 37° C.

IR (cm$^{-1}$): 3450 (COOH), 1730 (ring C=O), 1720 (COOH)

MS (m/e): 461 (M+), 416 (M+—COOH), 257 (M+—farnesyl group)

NMR (ppm): 1.48 (15H, bs, (CH$_3$—)×5), 1.87 (12H, m, (—CH$_2$CH$_2$—)×3), 4.48 (2H, bs, >NCH$_2$—), 4.84 (3H, m $$(\;\diagup\!\!\diagdown\underset{H}{\diagup\!\!\diagdown}\;)\times 3),$$

5.76 (1H, bd,

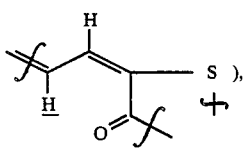

7.30 (1H, d, —CH=(Rh)), 7.99 (1H, bs, COOH)

EA for $C_{25}H_{35}NO_3S_2$ (MW=461.660): Calcd. (%): C 65.04; H 7.64; N 3.03; Found (%): C 65.31; H 7.80; N 2.95

EXAMPLE 14

[3-Carboxymethyl-5-(4-chloro-2-butenylidene)rhodanine sodium salt (sodium salt of Compound No.8)]

300 Milligrams of 3-carboxymethyl-5-(4-chloro-2-butenylidene)rhodanine obtained in Example 9 was dissolved into 10.8 ml of 0.1N sodium hydroxide aqueous solution and the resulting solution was freeze-dried to yield quantitatively the desired compound in the form of yellow powder.

The characteristic properties of the product are as follows:

MP: 270° to 273° (decomposition)
IR (cm$^{-1}$): 3130, 1735, 1682

The sodium salts of Compound Nos.1 to 7 and 9 to 12 were obtained in the same manner as described above.

EXAMPLE 15

[3-Carboxymethyl-5-(4-chloro-butenylidene)rhodanine potassium salt (potassium salt of Compound No.8)]

300 Milligrams of 3-carboxymethyl-5-(4-chloro-2-butenylidene)rhodanine was dissolved into 10.8 ml of 0.1N potassium hydroxide aqueous solution and the resulting solution was freeze-dried to yield quantitatively the desired compound in the form of light vermilion powder.

The characteristic properties of the product are as follows:

MP: 280° to 287° C. (decomposition)
IR (cm$^-$): 3130, 1736, 1679

The potassium salts of Compound Nos. 1 to 7 and 9 to 13 were obtained in the same manner as described above.

EXAMPLE 16

A mixture of 10 parts by weight of 3-carboxymethyl-5-(2-butenylidene)rhodanine (Compound No 7), 30 parts of lactose, 45 parts by weight of corn starch, 15 parts by weight of a microcrystalline cellulose (commercially available under the registered trade mark "Avicel" made by Asahi Chemical Industry Co., Ltd.), 3 parts by weight of methyl cellulose and 2 parts by weight of magnesium stearate was thoroughly blended and then screened through a 50 mesh screen. The resulting powder was tabletted by an automatic tabletting machine to give tablets containing 20 mg of the essential active ingredient per one tablet.

EXAMPLE 17

A mixture of 10 parts by weight of 3-carboxymethyl-5-(2-hexenylidene)rhodanine (Compound No.10), 55 parts by weight of lactose, 30 parts by weight of corn starch, 8 parts by weight of Avicel and 2 parts by weight of magnesium stearate was thoroughly blended. The mixture was then filled in capsules made of gelatin to give capsules containing 20 mg of the essential active ingredients per one capsule.

EXAMPLE 18

The tablets obtained in Example 16 were pulverized and the resulting powder was screened through a 50 mesh screen and a 100 mesh screen to give granules having a particle size of 5 to 100 meshes and containing 50 mg of the essential active ingredient per 1 g of granules.

EXAMPLE 19

The same mixture used in Example 17 was finely pulverized and then screened through a 100 mesh screen to give a powder having an average particle size of 100 meshes and containing 50 mg of the essential active ingredient per 1 g of powder.

EXAMPLE 20

[Platelet aggregation inhibiting activity]

The platelet aggregation inhibiting activity was examined with the rhodanine derivatives (I) of the present invention.

Test Method

Blood samples were collected from the auricular blood vessel of albino rabbits (white local breed), and washed platelets were prepared therefrom by the method of Baenziger et al. [N. L. Baenziger and P. W. Majerus, Methods in Enzymology, 31, 149 to 155 (1974)]. The platelets were suspended in a 15 mM Tris-hydrochloric acid buffer in a final concentration of $6 \times 10^8$ cells/ml (Tris: tris(hydroxymethyl)aminomethane). Each test compound was added thereto and incubation was carried out at 37° C. for 2 minutes. Then, the platelets were stimulated by addition of thrombin (final concentration 0.2 unit/ml; made by Mochida Pharmaceutical Co.) and the aggregation inhibiting activity was estimated by observation of the aggregation reaction using an aggregometer (made by Briston Co.).

The results obtained are shown in Table 2 in terms of IC$_{50}$ (50% inhibition concentration in M).

TABLE 2

| Compound No. | IC$_{50}$ (M) |
| --- | --- |
| 1 | $>3 \times 10^{-4}$ |
| 2 | $>3 \times 10^{-4}$ |
| 3 | $>3 \times 10^{-4}$ |
| 4 | $>3 \times 10^{-4}$ |
| 5 | $>3 \times 10^{-4}$ |
| 6 | $3 \times 10^{-5}$ |
| 7 | $2 \times 10^{-5}$ |
| 8 | $2 \times 10^{-5}$ |
| 9 | $>4 \times 10^{-4}$ |
| 10 | $3 \times 10^{-5}$ |
| 11 | $2 \times 10^{-5}$ |
| 12 | $>3 \times 10^{-4}$ |
| 13 | $4 \times 10^{-5}$ |
| Dipyridamole | $2 \times 10^{-4}$ |

As shown in Table 2, Compound Nos. 6, 7, 8, 10, 11 and 13 inhibited the thrombin-induced aggregation of washed rabbit platelets by 50% at a concentration of $2 \times 10^{-5}$ to $4 \times 10^{-5}$M. With other compounds, too, platelet aggregation inhibiting activity was observed, though it was weaker than that of the above six compounds. The activity of the above six compounds was about 10 times that of Dipyridamole, a platelet aggregation inhibitor in wide use.

EXAMPLE 21

[Aldose reductase inhibiting activity]

The aldose reductase inhibiting activity was examined with respect to the rhodanine derivative (I) of the present invention.

Test Method

The test was carried out according to the method of Hayman et al. [S. Hayman and J. H. Kinoshita, J. Biol. Chem., 240, 877 to 882 (1965)].

Thus, Wistar strain male rats were sacrificed by decapitation, the lenses were excised and homogenized with a 0.1M phosphate buffer [pH 6.8; containing 1 mM of mercaptoethanol and 1 mM of nicotinamide-adenine dinucleotide phosphate (NADP)]. The homogenate was then centrifuged at 10,000 g for 15 minutes and the supernatant was used as the crude enzyme solution.

Separately, a 0.1M phosphate buffer (pH 6.2) containing 0.104 mM of NADPH (reduced form of NADP) and 10 mM of DL-glyceraldehyde was prepared. To this buffer solution, there was added 15 μl of each of solutions of each test compound in varied concentrations, followed by addition of 25 μl of the crude enzyme solution prepared in advance, to thereby initiate the reaction. The decrease in absorbance at 340 nm was measured using a high-sensitivity self-registering spectrophotometer (Model SM-401 made by Union Giken Kabushiki Kaisha).

The results obtained are shown in Table 3 in term of $IC_{50}$ (50% inhibition concentration in M).

TABLE 3

| Compound No. | $IC_{50}$ (M) |
| --- | --- |
| 1 | $2 \times 10^{-7}$ |
| 2 | $1.4 \times 10^{-7}$ |
| 3 | $1 \times 10^{-7}$ |
| 4 | $3 \times 10^{-7}$ |
| 5 | $1.3 \times 10^{-7}$ |
| 6 | $7.5 \times 10^{-7}$ |
| 7 | $7 \times 10^{-8}$ |
| 8 | $1.3 \times 10^{-7}$ |
| 9 | $1 \times 10^{-7}$ |
| 10 | $4 \times 10^{-8}$ |
| 11 | $4.6 \times 10^{-8}$ |
| 12 | $7 \text{ to } 8 \times 10^{-8}$ |
| 13 | $6.5 \times 10^{-7}$ |

TABLE 3-continued

| Compound No. | $IC_{50}$ (M) |
| --- | --- |
| Sorvinyl (Note) | $2.0 \times 10^{-7}$ |

Note:
the registered trademark of
S—6-fluoro-spiro(chroman-4,4'-imidazolidine)-2',5'-dione having the following formula:

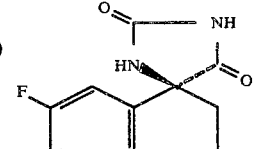

(made by Pfizer Inc.)

In the laboratory test for inhibitory activity against aldose reductase obtained from the rat eye lens, all the compounds listed in Table 3 showed 50% inhibition within the concentration range of $10^{-8}$ to $10^{-6}$M.

EXAMPLE 22

[Acute toxicity]

The acute toxicity in mice was examined with the rhodanine derivative (I) of the present invention.

Test Methed

To groups of 4 male ddY strain mice (5 weeks of age) were orally administered by gavage each test compound suspended in a 10% gum arabic and the mice were observed for death or survival for 2 weeks.

The results obtained with respect to Compound Nos. 7, 10, 11, 12 and 13 are shown in Table 4.

TABLE 4

| Oral dose (g/kg body weight) | Rate of death (%) |
| --- | --- |
| 1.0 | 0 |
| 2.5 | 0 |
| 3.5 | 0 |
| 5.0 | 100 |

As shown in Table 4, with respect to Compound Nos. 7, 10, 11, 12 and 13, $LD_{50}$ value (oral) was very high, namely in the range of 3.5 to 5.0 g/kg body weight.

It was thus demonstrated that the rhodanine derivatives (I) of the present invention are of very low toxicity.

As above results indicate, the rhodanine derivatives (I) of the present invention can be used as novel and highly safe therapeutic agents for diabetic complications which have not only potent platelet aggregation inhibiting activity but also aldose reductase inhibiting activity much more potent as compared with the known compounds having aldose reductase inhibiting activity.

In addition to the ingredients used in the Examples, other ingredients can be used in the Examples as set forth in the specification to obtain susbtantially the same results.

What we claim is:

1. A rhodanine compound having the following formula (I):

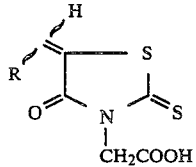

wherein R is t-butyl, 1,3-pentadienyl or 2,6-dimethyl-1,5-heptadienyl; or a nontoxic salt thereof.

2. A pharmaceutical composition as a therapeutic agent for diabetic complications which comprises as an essential active ingredient an effective amount of a rhodanine compound having the following formula (I):

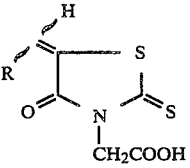

wherein R is t-butyl, 1,3-pentadienyl or 2,6-dimethyl-1,5-heptadiene; or a nontoxic salt thereof.

* * * * *